United States Patent [19]

Mueller

[11] Patent Number: 5,514,172

[45] Date of Patent: May 7, 1996

[54] MULTI-CONDUCTOR LEAD INCLUDING A CONNECTOR WITH AN INTERLOCKING INSULATOR

[75] Inventor: David E. Mueller, Santa Clarita, Calif.

[73] Assignee: Pacesetter, Inc., Sylmar, Calif.

[21] Appl. No.: 299,702

[22] Filed: Aug. 31, 1994

[51] Int. Cl.⁶ .................................................. A61N 1/05
[52] U.S. Cl. ...................... 607/122; 607/119; 607/116; 128/639
[58] Field of Search ................................. 607/116, 122, 607/119; 128/639

[56] References Cited

U.S. PATENT DOCUMENTS

| 3,774,497 | 11/1973 | Stahl | 87/55 |
| 4,142,532 | 3/1979 | Ware | 128/419 R |
| 4,228,889 | 10/1980 | Garrison | 198/501 |
| 5,016,646 | 5/1991 | Gotthardt et al. | 607/122 |
| 5,304,219 | 4/1994 | Chernoff et al. | 607/116 |
| 5,354,327 | 10/1994 | Smits | 607/122 |

OTHER PUBLICATIONS

Doring et al, "The Impact of Pending Technologies on a Universal Connector Standard", i PACE, Nov.–Dec. 1986, pp. 1186–1190.

*Primary Examiner*—William E. Kamm
*Assistant Examiner*—Carl H. Layno
*Attorney, Agent, or Firm*—Lisa P. Weinberg

[57] ABSTRACT

A multi-conductor lead having a lead body including at least two conductors and at least one electrode at a distal end for delivering an electrical stimulus, the multi-conductor lead also including a connector assembly at a proximal end, the connector assembly including a pair of electrical contacts each connected to one of the two conductors of the multi-conductor lead and a rigid insulator interlocking and electrically separating the pair of electrical contacts.

24 Claims, 5 Drawing Sheets

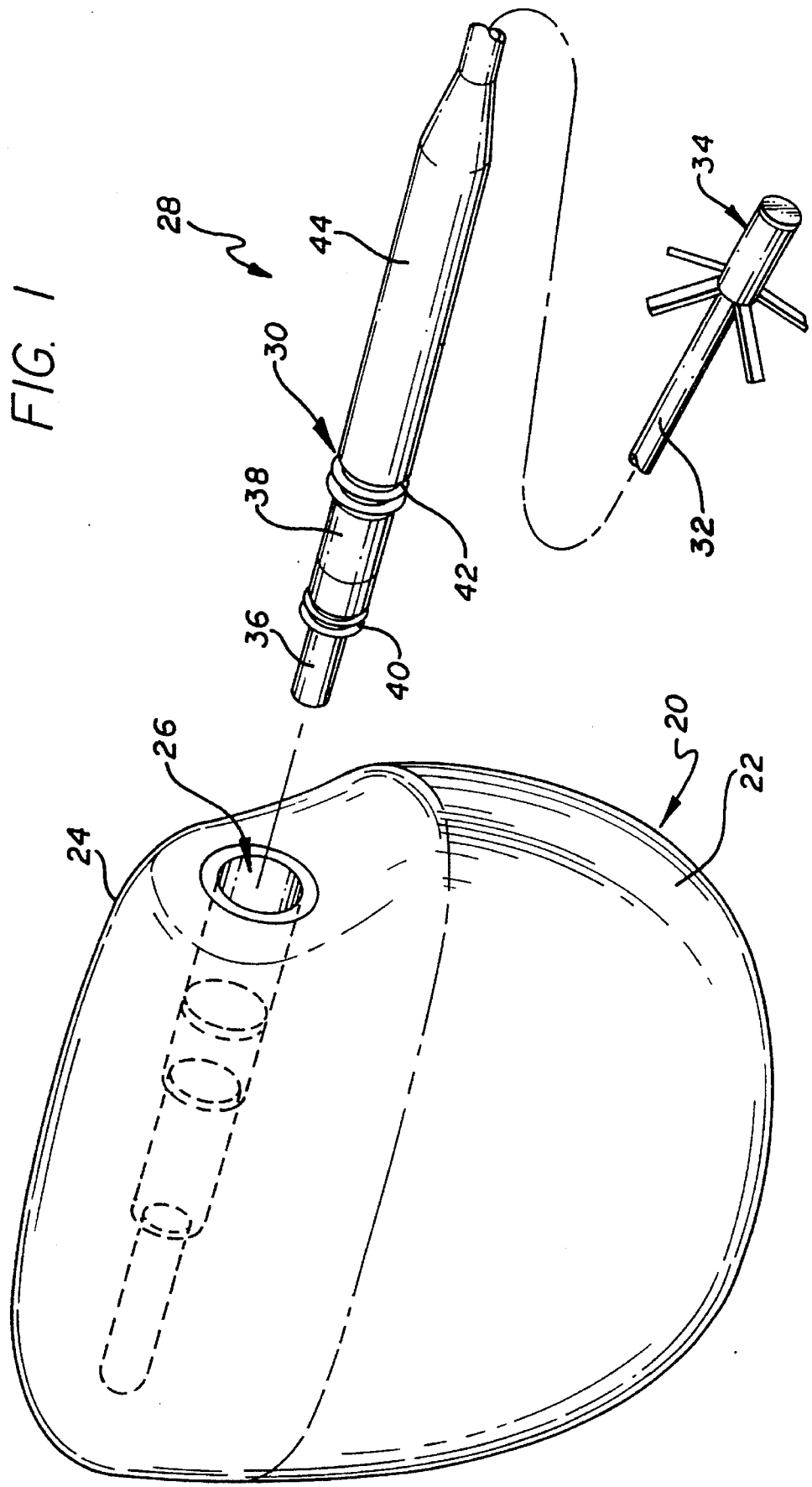

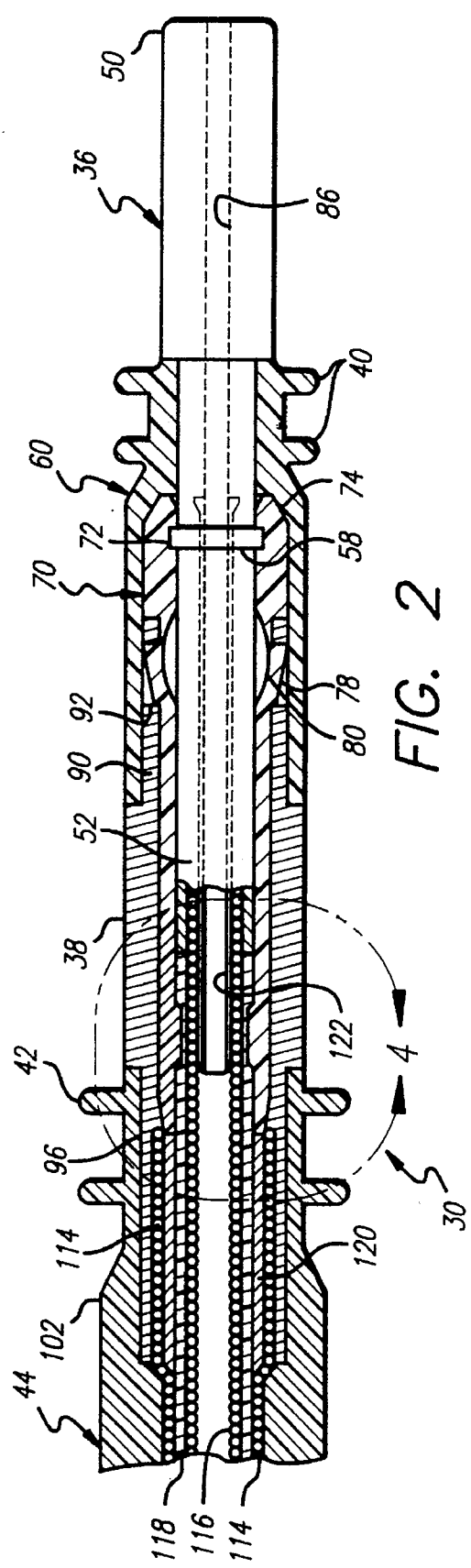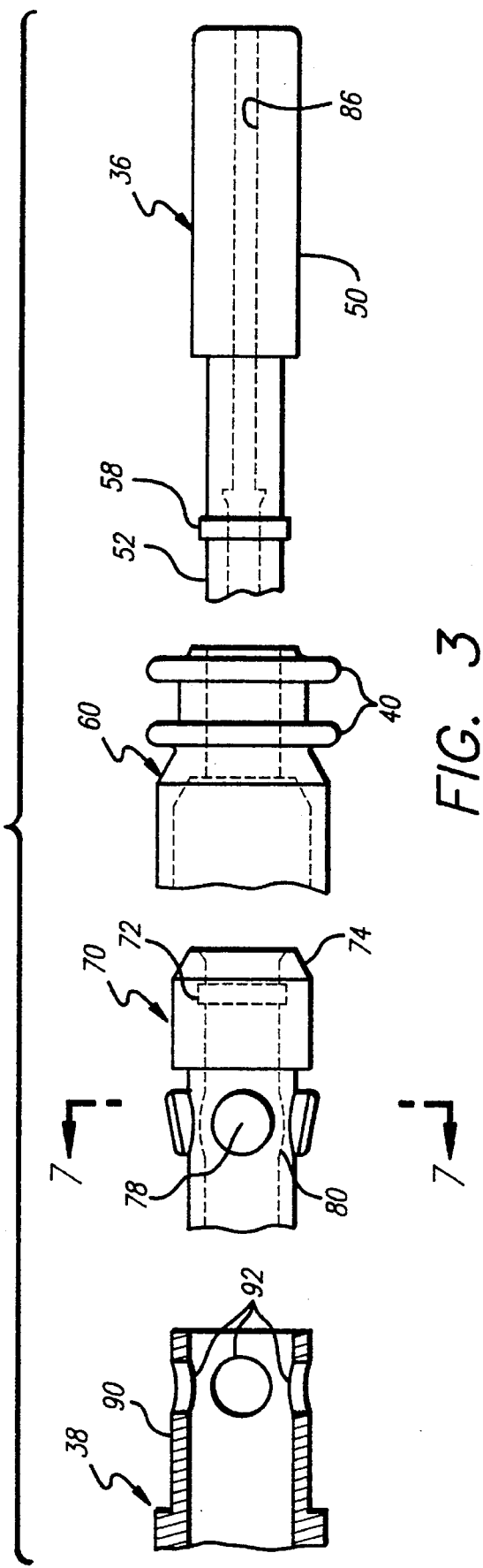

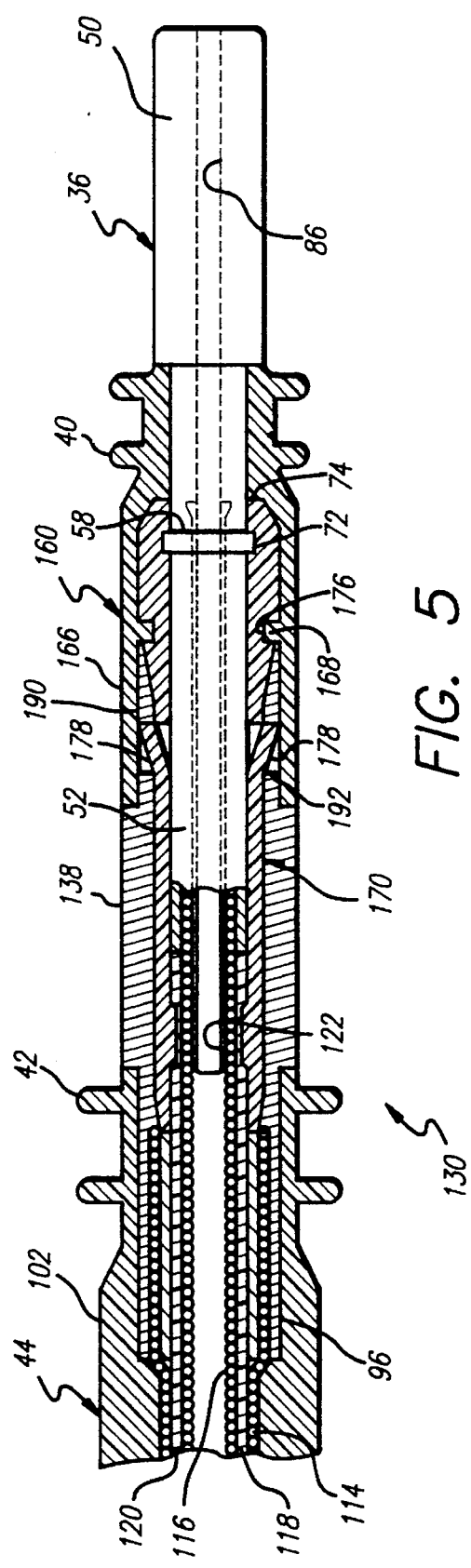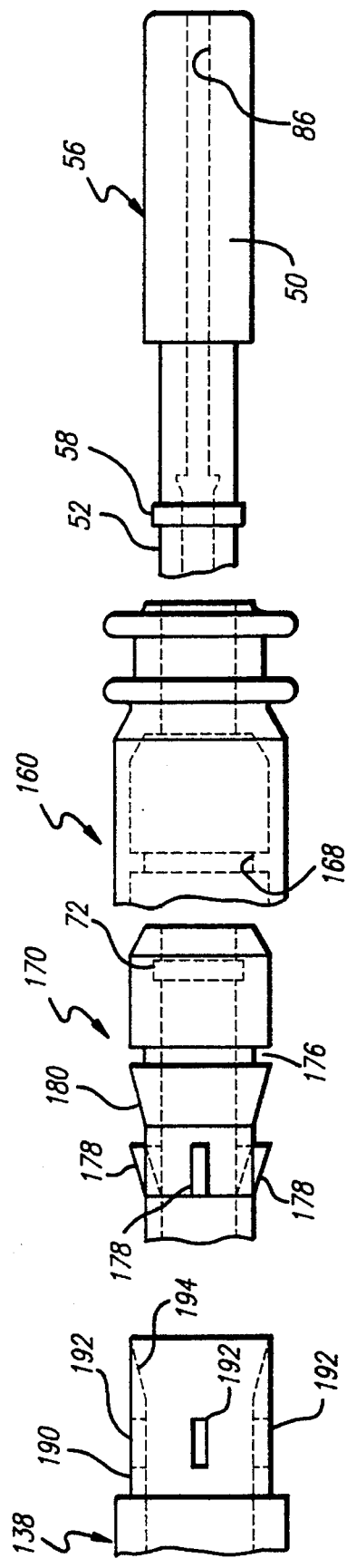

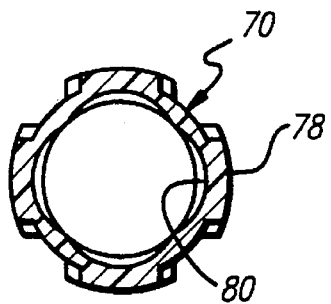
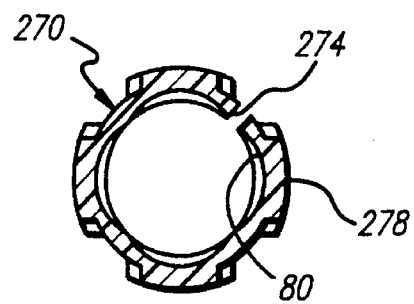
FIG. 7
FIG. 8
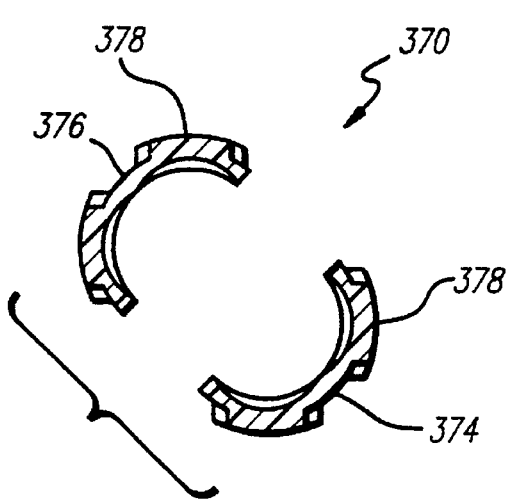
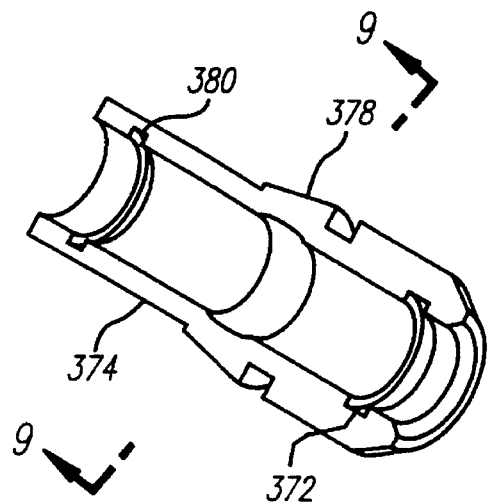
FIG. 9
FIG. 10
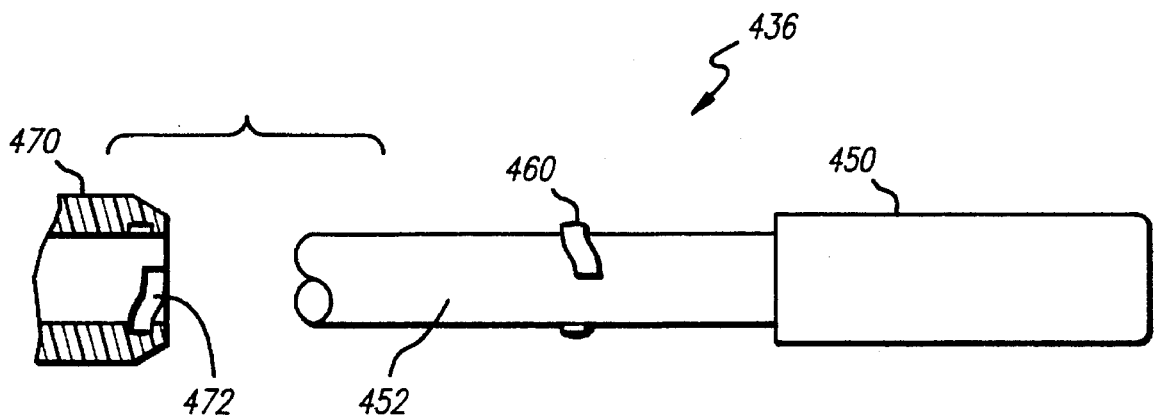
FIG. 11

MULTI-CONDUCTOR LEAD INCLUDING A CONNECTOR WITH AN INTERLOCKING INSULATOR

FIELD OF THE INVENTION

The invention relates to implanted medical devices and connectors for coupling a lead, such as a cardiac pacing lead, to an implanted pulse generator, and more particularly to a connector assembly having an interlocking insulator which prevents degradation and shorting between conductors in the lead.

BACKGROUND OF THE INVENTION

Implantable electronic devices are in use providing electronic pulses to stimulate tissue via a lead extending from an implanted pulse generator to a desired internal location. An example of this type of technology is a pacemaker and a pacing lead which provides electrical stimulation to the heart. The pacemaker is usually implanted in a subcutaneous cavity, and the leads extend either transvenously to the internal cavities of the heart, or to patch electrodes located on external surface of the heart.

The leads generally include at least one and often two or more electrodes located at a distal end, and a connector having a similar number of electrical connector elements for interconnection to the pulse generator at the proximal end. The electrical connector elements at the proximal end and the distal electrodes are interconnected by conductors extending through an insulated lead body. It is common for the leads to include helically wound conductors which are either coaxially mounted or side-by-side wound within the lead body, separated by insulation.

The connector is inserted into a receiving orifice in a header portion of the pulse generator. The header portion of the pulse generator may be formed from an epoxy material which is assembled and bonded to the main body of the pulse generator. The main body of the pulse generator is generally a metallic self-contained housing or can, which encloses the source of electrical energy and electrical circuitry for controlling the electrical stimulus delivered by the lead.

In the design of the lead connector and the pulse generator, it is important for the lead to be safely secured to the pulse generator to prevent inadvertent decoupling. Generally, connectors have been assembled using flexible insulation materials to separate the respective electrical components. Problems which arise in the construction and use of multiple conductor lead connectors are primarily related to the design of the electrical interconnection between the conductors and the contacts. The connector must be constructed in a manner which prevents fluids from invading the connector and shorting the electrical conductors therein.

One inherent physical weakness of small pacemaker lead connectors (i.e. VS-1 and IS-1 standard) is bond failure between conductor and insulation laminations. Traditional coaxial connectors transmit most mechanical stress between material layers during tensile or torsional loading. Present lead designs rely on chemical bonds between these layers to withstand this stress. Bonding or molding of traditional lead construction is very process sensitive and can be weakened by assembly process contamination or can fail after implant due to hydrolyzation of the bond interface.

It would be beneficial to have a lead assembly including a connector assembly featuring an improved structural interconnection between the conductors and the electrical connectors, and having increased resistance to failures from invasion of fluids.

SUMMARY OF THE INVENTION

The present invention is directed to a pacing lead having an improved connector assembly, and more particularly to a multipolar coaxial lead having a rigid insulating element formed to act as both an insulator separating the coaxial conductors and a mechanical fastener to secure the electrical connector elements to one another in a consistently strong assembly.

BRIEF DESCRIPTION OF THE DRAWINGS

FIG. 1 depicts a perspective view of the components of a pacing system;

FIG. 2 depicts a partial cross-sectional view of the connector assembly of the pacing lead of FIG. 1;

FIG. 3 depicts a partial exploded view of the connector assembly of FIGS. 1 and 2;

FIG. 5 depicts a partial cross-sectional view of an alternative embodiment of the connector assembly of the pacing lead of FIG. 1;

FIG. 6 depicts a partial exploded view of the connector assembly of FIG. 5;

FIG. 7 is a cross-sectional view through the rigid insulator element of FIG. 3 taken along line 7—7;

FIG. 8 is a cross-sectional view of an alternative design for the rigid insulator of FIG. 7;

FIG. 9 is a cross-sectional view of another alternative design for the rigid insulator of FIG. 7;

FIG. 10 is a perspective view of one of the two elements forming the rigid insulator of FIG. 9; and FIG. 11 is an alternative design for a locking mechanism for the connector assembly of FIG. 2.

DETAILED DESCRIPTION OF THE PREFERRED EMBODIMENTS

Figure 4:
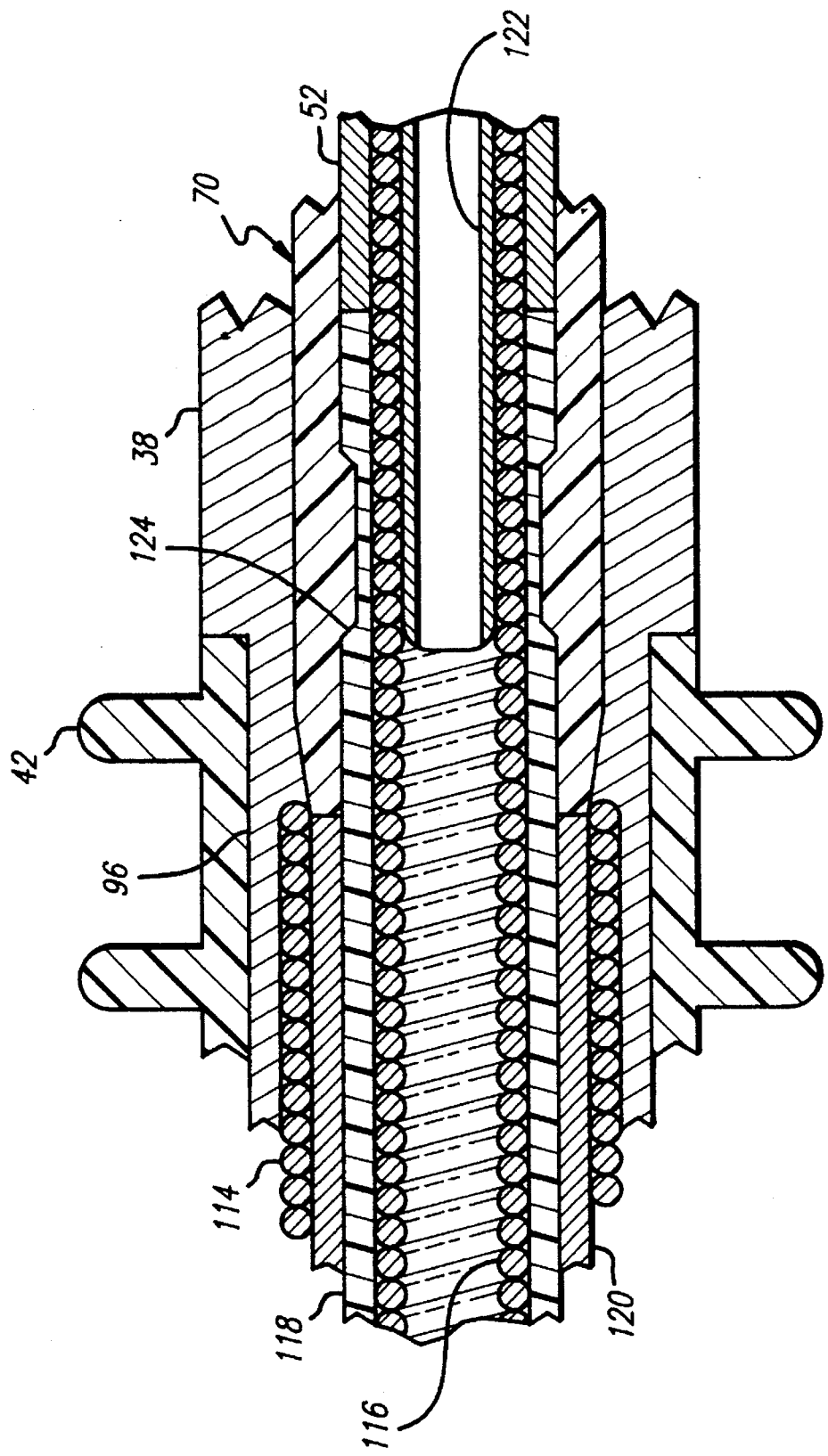
FIG. 4 depicts an enlarged view of a portion of the connector assembly of FIG. 2.

FIG. 1 depicts an implantable medical device including a pulse generator 20 such as a pacemaker, which includes a hermetically sealed metallic housing 22 containing the power supply and electronic circuitry (not shown) of the pulse generator 20, and an attached header 24 including at least one connector receiving orifice 26. The header 24 may be either integral with the housing 22, or formed as a separate element and attached to the housing 22. It should be noted that the pulse generator 20 may have two or more orifices for receiving the connectors of two or more leads, if required.

Also depicted in FIG. 1 is a pacing lead 28 including a connector assembly 30 at the proximal end designed to be inserted into the receiving orifice 26 of the pulse generator 20. The pacing lead 28 further includes a lead body 32 extending from its proximal end connection to the connector assembly 30 to an electrode assembly 34 at the distal end of the lead body 32. The electrode assembly 34 is designed to deliver electrical stimulus to the implant situs. While the design of the connector assembly 30 detailed herein is described in connection with a pacing lead, it should be pointed out that the connector assembly 30 can be incorporated into other types of leads, such as sensor leads and defibrillation leads having differing electrode assemblies.

As illustrated in FIGS. 1 and 2, the connector assembly 30 includes a pair of electrical contact elements, such as a pin connector 36 and a ring connector 38, as well as seals 40 and 42, and a lead boot 44. FIG. 2 depicts a partial cross-sectional view of the connector assembly 30 detailing the design of the subcomponents which comprise the proximal portion of the connector assembly 30.

Proceeding distally from the pin connector 36, illustrated at the right portion of the FIG. 2, the pin connector 36 includes a generally cylindrical head portion 50 and a reduced diameter tail portion 52. The tail portion 52 projects into the connector assembly 30 and more specifically into a hollow, generally cylindrical insulation element 60 which includes the seals 40 on an outer surface, as well as into a proximal end of a rigid insulator 70. The tail portion 52 of pin connector 36 includes one or more circumferential ridge(s) 58 which allow interlocking of the pin connector 36 to the radially adjacent rigid insulator 70 within the connector assembly 30.

The rigid insulator 70 is configured as a generally cylindrical element having a circumferential recess 72 on its inner surface located near its proximal end 74. The tail portion 52 of pin connector 36 extends axially into the center of the rigid insulator 70, so that the circumferential recess 72 receives the circumferential ridge 58 of the pin connector 36. The insulation element 60 may also be bonded to the pin connector 36 and rigid insulator 70 with a biocompatible adhesive.

The distal end of the rigid insulator 70 is inserted axially into the ring connector 38. The ring connector 38 has a stepped exterior profile, wherein respective axial ends have a diameter which is less than the diameter of the central portion defining the electrical contact of the ring connector 38. Thus, the proximal end of the ring connector 38 defines a sleeve 90 which is inserted axially into the insulation element 60, and may be bonded thereto by a biocompatible adhesive. In addition, the sleeve 90 of ring connector 38 includes one or more spaced apart slots or circular holes 92, operative to retain the rigid insulator 70 in place, as discussed below.

The rigid insulator 70 includes at least one and preferably several radially projecting scallop shaped or circular elements 78. Each of the circular elements 78 extends at an angle radially outward from its distal side to its proximal side. The circular elements 78 are formed integrally with the rigid insulator 70, and are capable of deflecting radially inward during insertion into the ring connector 38. The defection of the circular elements 78 may be facilitated by relieving the radially inner surface of the rigid insulator 70 as shown by recesses 80. Following insertion of the rigid insulator 70 into the ring connector 38, the circular holes 92 accept the circular elements 78, which spring out to their original shape. The combination of the circular elements 78 fitting into and being retained in the holes 92 locks the rigid insulator 70 axially in place with respect to the ring connector 38.

Accordingly, due to the locking engagement of the ring connector 38 with the rigid insulator 70, as well as the locking engagement of the pin connector 36 with the rigid insulator 70, the primary subcomponents of the connector assembly 30 are axially locked in place with respect to one another.

Returning to the ring connector 38, a distal tail 96, having a reduced diameter from that of the center of the ring connector 38, extends axially into a generally cylindrical insulator 102 forming the lead boot 44. The distal tail 96 of the ring connector 38 surrounds a first helical conductor 114, and is electrically secured thereto. In addition, a second helical conductor 116 is radially spaced from the first helical conductor 114 by a cylindrical insulator 118. A cylinder 120 formed from a rigid material which is preferably electrically conductive, is inserted over the cylindrical insulator 118 forcing the first helical conductor 114 radially outward and into secure electrical contact with the distal tail 96 of the ring connector 38. The distal tail 96 may be further secured to the first helical conductor 114 by crimping. The distal end of the rigid insulator 70 abuts against the cylinder 120, which itself extends approximately the same distance into the lead boot 44 as the distal tail 96 of the ring connector 38, and the first helical conductor 114 terminates at about the distal end of the rigid insulator 70.

The second helical conductor 116 and a portion of the cylindrical insulator 118 extend axially into the distal end of rigid insulator 70. The tail portion 52 of the pin connector 36 is inserted over the second helical conductor 116 within the rigid insulator 70, so that the end of the tail portion 52 abuts against the proximal end of the cylindrical insulator 118.

FIG. 3 depicts a partial exploded view of portions of the ring connector 38, rigid insulator 70, insulation element 60, and pin connector 36. As depicted at the right side of FIG. 3, the pin connector 36 is illustrated with the circumferential ridge 58 on the outer diameter of the tail portion 52. Pin connector 36 also includes axial bore 86 extending through its entire length, to allow insertion of a stylet (not shown).

Upon insertion of pin connector 36 into rigid insulator 70, the rigid insulator 70 will deform at the proximal end until the circumferential ridge 58 on pin connector 36 seats in the circumferential recess 72 of rigid insulator 70. Upon insertion of the rigid insulator 70 into the ring connector 38, the rigid insulator 70 will deform at the circular elements 78 until the circular elements 78 can spring radially outward into the circular holes 92. The tops of the circular elements 78 are preferably inclined to facilitate assembly through the axial bore of the ring connector 38. The resilient insulation element 60 fits snugly over the end of the rigid insulator 70 and sleeve 90 of ring connector 38, and is preferably bonded thereto by a medical adhesive (not shown).

Preferably, the thickness of the rigid insulator 70 is greater than the cylinder defined between the outer diameter of insulation 118 supported on the internal diameter by the second helical conductor 116, and the internal diameter of ring connector 38. Thus, following assembly, a compression fit results which further secures the elements of the connector assembly 30 together axially, to prevent them from separating. The compression fit of the rigid insulator 70 also acts as a mechanical wedge along the respective portions of the pin connector 36 and inner surface of ring connector 38. In addition, biocompatible adhesives can be used during assembly to bond or provide additional fluid seal between the components of the connector assembly 30.

FIG. 4 depicts an enlarged partial cross-sectional view of the construction of the connector assembly 30 shown within circle 4—4 of FIG. 2. The partial cross-sectional view of FIG. 4 better illustrates the assembled configuration for the electrical interconnections between pin connector 36 and the second helical conductor 116, as well as ring connector 38 and the first helical conductor 114. Also illustrated are the distal ends of the second cylinder 122 as well as the distal end of rigid insulator 70, and the proximal end of cylindrical insulator 118 which separates the respective helical conductors 116 and 114.

The second cylinder 122 acts to force the second helical conductor 116 outward into secure electrical contact with the inner diameter of the tail portion 52 of pin connector 36. The tail portion 52 of pin connector 36 may also be further secured to the second helical conductor 116 by crimping. As illustrated, the helical conductor 116 may have its inner diameter supported by the distal end of second cylinder 122. In addition, the rigid insulator 70 may include an internal shoulder 124 which squeezes the cylindrical insulator 118 between itself and the more rigid helical conductor 116. This design tends to secure the rigid insulator to the proximal end of the helical conductor 116, as well as assists in securing the electrical contact between the pin connector 36 and the second helical conductor 116.

FIGS. 5 and 6 depict a connector assembly 130 having selected alternative features which may be incorporated into the connector assembly 30 of FIG. 1. In FIGS. 5 and 6, those elements or features which are identical to the elements detailed in the above discussion of FIGS. 2 and 3 are identified with the same element number and the foregoing description is incorporated with respect to FIGS. 5 and 6. However, modified elements and new features are designated by new numbers in the one-hundred series, and are discussed below.

The principal modifications in the connector assembly 130 of FIGS. 5 and 6 are in the ring connector 138, insulator element 160 and rigid insulator 170, which are illustrated in the exploded view of FIG. 6. Specifically, the sleeve 190 of ring connector 138 includes one or more axially aligned slots 192, replacing the circular holes 92 of FIGS. 2 and 3. In addition, the inner diameter of the sleeve 190 of ring connector 138 may include a bevel 194 to aid insertion of the rigid insulator 170.

The rigid insulator 170 includes one or more tabs 178 which are cutout and flared outward, so that tabs 178 will project into the slots 192 upon insertion of the rigid insulator 170 into the ring connector 138. The rigid insulator 170 may also include a bevelled surface 180 to closely fit the bevel 194 at the end of the ring connector 138. In addition, the rigid insulator 170 may also include a circumferential recess 176 on its outer surface which receives an internal ridge 168 formed on the inner diameter of a sleeve portion 166 of the insulation element 160, to lock the insulation element 160 to the rigid insulator 170.

The rigid insulators 70 or 170 of FIGS. 2–6 are preferably formed from a rigid biocompatible material. Suitable materials for the rigid insulators include polysulfone and plastics, and particularly a polyether polyurethane elastomer having a hardness of at least 50 on the ASTM D-2240 test scale. It should be noted that it is also beneficial for the material of the rigid insulators to be somewhat pliant at temperatures well above normal body temperatures, such that the rigid insulator may be heated before assembly of the connector assembly, to facilitate insertion of the rigid insulator and deformation of the circular elements 78 or tabs 178, during insertion into the ring connector 38 (or 138).

The insulation elements 60 and 160 of FIGS. 2–6 are preferably formed from a resilient biocompatible material capable of returning to an original shape following deformation, even after prolonged exposure to the intended implanted environment. The resilient biocompatible material of the insulation elements may be a platinum cured silicone rubber or polyurethane, or similar material.

FIG. 7 depicts a cross-sectional view through the rigid insulator 70 along lines 7—7 of FIG. 3. In addition to depicting the generally cylindrical shape of the rigid insulator 70, the portions of the circular elements 78 extending radially outwardly from the cylinder are depicted, as are the recesses 80.

FIG. 8 depicts an alternative configuration for a rigid insulator 270 taken along the same line 7—7 of FIG. 3 as the illustration of FIG. 7. In FIG. 8, the rigid insulator 270 includes an axial cut 274 which runs the entire length of the rigid insulator 270. The rigid insulator 270 is identical to rigid insulator 70 of FIGS. 2 and 3. The axial cut 274 is preferably located between two of the respective circular elements 278. The axial cut 274 allows the rigid insulator 270 to be expanded during installation over the tail portion 52 of pin electrode 36 (FIGS. 2 and 3), thereby making it easier to assemble over the circumferential ridge 58 during installation. Following completion of assembly, as for example illustrated in FIG. 2, the axial slot 274 will be held closed within the inner diameter of ring electrode 38.

FIGS. 9 and 10 depict a second alternative embodiment of a rigid insulator 370. FIG. 9 is a cross-section taken generally along line 9—9 of FIG. 10 and is generally the same as line 7—7 of FIG. 3 shown in the illustration of FIG. 7. In FIG. 9, the rigid insulator 370 is divided into two essentially symmetrical elements 374 and 376, each of which generally forms a half cylinder. When mated together, symmetrical elements 374 and 376 define the cylindrical rigid insulator 370. The rigid insulator 370 is thus divided on a diagonal line passing through the rigid insulator 370 so as to not cut the respective circular elements 378, depicted on the outer surface of the rigid insulator 370. Again, as in the case of the rigid insulator 270 of FIG. 8, upon assembly of the rigid insulator 370 about the tail portion 52 of pin connector 36 (FIGS. 2 and 3), the respective symmetrical elements 374 and 376 of rigid insulator 370 are held together within the ring electrode 38.

FIG. 10 depicts a perspective view of one of the symmetrical elements 374 which constitute the rigid insulator 370. The rigid insulator 370 is essentially identical to the rigid insulator 70 of FIGS. 2 and 3. As depicted in FIG. 10, in addition to the projecting circular elements 378, the symmetrical element 374 includes a circumferential slot 372 located so as to accept the circumferential ridge 58 of pin connector 36 as depicted in FIGS. 2 and 3. In addition, the symmetrical element 374 may include a recessed slot 380 on its inner diameter located near the distal end. This slot 380 may accommodate a shoulder formed when a compressive force is exerted on the relatively pliant cylindrical insulator 118 of FIGS. 2 and 4, to thereby aid in securing the rigid insulator 370 to the cylindrical insulator 118.

FIG. 11 depicts an alternative locking assembly for interengaging a pin connector 436 and a rigid insulator 470, which may replace the respective pin connector 36 and rigid insulator 70 of FIGS. 2 and 3. According to the construction shown in FIG. 11, a tail portion 452 of pin connector 436 includes partial threads 460 which are accommodated by internal channels 472 located within the rigid insulator 470. In this manner, the partial threads 460 may be aligned and then rotated into the channels 472 to threadably lock or secure the pin connector 436 and the rigid insulator 470 together. The design according to FIG. 11 provides an exemplary replacement for the circumferential ridge 58 depicted in FIGS. 2 and 3 and its respective circumferential recess 72 on the rigid insulator 70. It may be appreciated, however, that other mechanisms of interengaging and then locking a pin connector to a rigid insulator such as 70 may be contemplated to replace those described and depicted in the figures herein.

The connector assemblies according to the present invention exhibit an enhanced pull strength due to the construction and incorporation of the rigid insulator which mechanically locks the pin connector 36 and the ring connector 38.

Thus, as compared to the current pull strength standard of 2.2 lbs., the connector assembly of the present invention has a pull strength in excess of 4 lbs. This enhancement is particularly advantageous in that if an implanted device such as a pacemaker must be replaced, it is less likely that the lead having a connector assembly as detailed above will be damaged during its removal from the implanted device.

It should be evident from the foregoing description that the present invention provides advantages over pacing leads and connector assemblies of the prior art. Particularly, further equivalent variations for the locking mechanisms between the rigid insulator and electrical connectors may be devised. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. An implantable lead for delivering an electrical stimulus from a pulse generator to tissue, the implantable lead comprising:

a lead body having at least two conductors extending from a distal end to a proximal end of said lead body;

at least one electrode located at the distal end of said lead body and connected to at least one of said conductors;

a connector assembly located at the proximal end of said lead body, said connector assembly including a pair of electrical connectors each attached to one of said at least two conductors of said lead body;

a rigid insulator disposed between said pair of electrical connectors of said connector assembly in relative position; and interlocking mechanism means for interlocking at least one of said pair of electrical connectors to said rigid insulator.

2. The implantable lead of claim 1, wherein said rigid insulator comprises a rigid biocompatible material having a hardness of at least 50 on the ASTM D-2240 test scale.

3. The implantable lead of claim 2, wherein said rigid biocompatible material is selected from the group consisting of polysulfone and plastic.

4. The implantable lead of claim 1, wherein said pair of electrical connectors further includes a pin connector located at a proximal tip of said connector assembly, and a ring connector located distally of said proximal tip, wherein said interlocking mechanism means comprises:

means for interlocking said pin connector and said rigid insulator; and means for interlocking said ring connector and said rigid insulator.

5. The implantable lead of claim 4, wherein said means for interlocking said pin connector and said rigid insulator comprises:

at least one ridge located on said pin connector; and at least one internal recess on said rigid insulator sized to receive said at least one ridge located on said pin connector.

6. The implantable lead of claim 5, further comprising:

an insulation sleeve element mounted about a portion of said pin connector, said insulating means, and a portion of said ring connector, said insulation sleeve element having at least one internal ridge; and an external recess on said rigid insulator sized to receive said internal ridge of said insulation sleeve element.

7. The implantable lead of claim 4, wherein said means for interlocking said ring connector and said rigid insulator comprises:

at least one element projecting outwardly from said rigid insulator; and at least one orifice on said ring electrode sized to receive said at least one element projecting from said rigid insulator.

8. The implantable lead of claim 4, wherein said pin connector is electrically coupled to one of said at least two conductors of said lead body and said ring connector is electrically coupled to another of said at least two conductors of said lead body.

9. The implantable lead of claim 8, further comprising:

a cylindrical insulator extending from said proximal end to said distal end of said lead body, said cylindrical insulator radially separating said conductor electrically coupled to said pin connector and said conductor electrically coupled to said ring connection; and a sleeve inserted axially over a proximal end of said cylindrical insulator to displace said conductor electrically coupled to said ring connector radially outward into secure contact with said ring connector.

10. The implantable lead of claim 4, wherein said rigid insulator comprises a material having properties equivalent to polysulfone.

11. The implantable lead of claim 4, further comprising a biocompatible adhesive interbonding adjacent surfaces of said pin connector, said rigid insulator, and said ring connector.

12. The implantable lead of claim 6, further comprising a biocompatible adhesive interbonding adjacent surfaces of said pin connector, said rigid insulator, said ring connector, and said insulation sleeve element.

13. The implantable lead of claim 1, wherein said connector assembly further comprises:

an insulation tubing sleeve located over a radially inner conductor of said at least two conductors insulating it from a radially outer conductor of said at least two conductors along the entire length of the outer conductor; and means for securing said insulation tubing to said rigid insulator.

14. A multi-conductor lead having a lead body including at least two conductors extending from a proximal end to a distal end of said lead body and at least one electrode at the distal end for delivering an electrical stimulus, the multi-conductor lead also including a connector assembly at the proximal end, the connector assembly comprising:

a pair of electrical contacts each connected to one of the at least two conductors of the multi-conductor lead;

a rigid insulator electrically separating said pair of electrical contacts; and interlocking mechanism means for interlocking at least one of said pair of electrical contacts to said rigid insulator.

15. The multi-conductor lead of claim 14, wherein said pair of electrical contacts of said connector assembly further comprise:

a pin connector located at a proximal tip of said connector assembly; and a ring connector located distally of said proximal tip of said connector assembly.

16. The multi-conductor lead of claim 15, wherein said interlocking mechanism means comprises:

at least one ridge located on a distal portion of said pin connector; and at least one internal recess on said rigid insulator sized to receive said at least one ridge of said pin connector to mechanically lock said pin connector to said rigid insulator.

17. The multi-conductor lead of claim 15, wherein said interlocking mechanism means comprises:

at least one element projecting radially from said rigid insulator; and at least one orifice on said ring connector to receive said at least one element projecting radially from said rigid insulator, said at least one element projecting from said rigid insulator operative with said at least one orifice to mechanically lock said ring connector and said rigid insulator axially.

18. The multi-conductor lead of claim 15, wherein said interlocking mechanism means comprises:

means for locking said pin connector to said rigid insulator; and means for locking said ring connector to said rigid insulator.

19. The multi-conductor lead of claim 17, wherein said connector assembly further comprises:

an insulation tubing sleeve located over a radially inner conductor of said at least two conductors insulating it from a radially outer conductor of said at least two conductors along their entire length; and means for securing said insulation tubing to said rigid insulator.

20. The multi-conductor lead of claim 18, wherein said connector assembly further comprises:

a biocompatible adhesive interbonding said pin connector, said rigid insulator, and said ring connector.

21. The multi-conductor lead of claim 18, wherein said connector assembly further comprises:

an insulation sleeve element coaxially mounted about portions of said pin connector and said rigid insulator; and means for axially locking together said insulation sleeve element and said pin connector.

22. The multi-conductor lead of claim 14, wherein said connector assembly has a pull strength greater than 4 lbs.

23. The multi-conductor lead of claim 21, wherein said rigid insulator is split axially to facilitate assembly.

24. The multi-conductor lead of claim 21, wherein said rigid insulator further comprises:

a pair of generally half-cylindrical symmetrical elements.

* * * * *